United States Patent [19]
Mederski et al.

[11] Patent Number: 5,405,964
[45] Date of Patent: Apr. 11, 1995

[54] IMIDAZOPYRIDINES

[75] Inventors: Werner Mederski, Erzhausen; Dieter Dorsch, Ober-Ramstadt; Andreas Bathe, Griesheim; Thorsten Hartig, Gross-Zimmern; Mathias Osswald, Zwingenberg; Norbert Beier, Reinheim; Pierre Schelling, Mühltal; Klaus-Otto Minck, Ober-Ramstadt; Ingeborg Lues, Darmstadt, all of Germany

[73] Assignee: Merck Patent Gesellschaft mit beschrankter Haftung, Darmstadt, Germany

[21] Appl. No.: 139,668

[22] Filed: Oct. 22, 1993

[30] Foreign Application Priority Data

Oct. 24, 1992 [DE] Germany .......... 42 36 026.9

[51] Int. Cl.$^6$ .................. C07D 471/02; C07D 471/04; C07D 471/06
[52] U.S. Cl. .................................................. 546/118
[58] Field of Search .................... 514/303; 546/118

[56] References Cited

U.S. PATENT DOCUMENTS

| | | |
|---|---|---|
| 4,880,804 | 11/1989 | Carini et al. .............. 514/231.5 |
| 5,036,048 | 7/1991 | Watkins ...................... 514/16 |
| 5,177,074 | 1/1993 | Allen et al. ................. 514/234.2 |

FOREIGN PATENT DOCUMENTS

| | | |
|---|---|---|
| 0480204 | 4/1992 | European Pat. Off. . |
| 0505893 | 9/1992 | European Pat. Off. . |
| 0513979 | 11/1992 | European Pat. Off. . |
| 91/14367 | 10/1991 | WIPO . |
| 91/19697 | 12/1991 | WIPO . |

*Primary Examiner*—C. Warren Ivy
*Assistant Examiner*—D. Margaret M. Mach
*Attorney, Agent, or Firm*—Millen, White, Zelano & Branigan

[57] ABSTRACT

Novel imidazopyridine derivatives of formula I

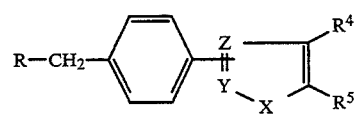

wherein
R is

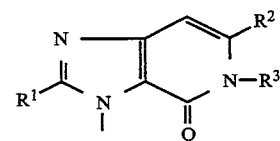

and X, —Y=Z—, $R^1$, $R^2$, $R^3$, $R^4$ and $R^5$ as defined herein, and their salts, exhibit antagonistic properties towards angiotensin II and can be used for the treatment of hypertension, aldosteronism, cardiac insufficiency and increased intraocular pressure, and of disorders of the central nervous system.

5 Claims, No Drawings

IMIDAZOPYRIDINES

The invention relates to novel imidazopyridine derivatives of formula I

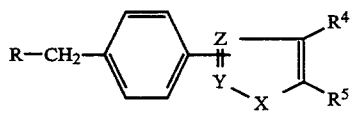

wherein
R is

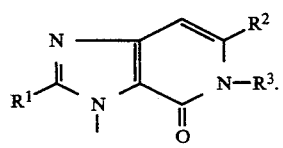

X is O, S or NR$^6$,
—Y=Z— is

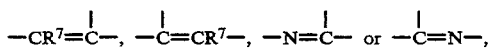

R$^1$ is A, alkenyl or alkynyl each having up to 6 C atoms, cycloalkyl having 3–7 C atoms, OA or SA,
R$^2$ is H or Hal,
R$^3$ is H, R$^8$ or —C$_n$H$_{2n}$—R$^9$,
R$^4$ and R$^5$ are each H, A or Hal,
R$^6$ is H or —C$_m$H$_{2m}$—R$^{10}$,
R$^7$ and R$^{10}$ are each CN, COOR$^{11}$ or 1H-5-tetrazolyl,
R$^8$ is alkyl having 1–6 C atoms wherein one or more H atoms can also be replaced by F,
R$^9$ is COOR$^{12}$, CONR$^{12}$R$^{13}$, COA, NR$^{12}$R$^{13}$, cycloalkyl having 3–7 C atoms, Ar, Her, COAr or CO-Het,
R$^{11}$, R$^{12}$ and R$^{13}$ are each H, A or Ar,
A is alkyl having 1–6 C atoms,
Ar is an unsubstituted phenyl group or a phenyl group which is monosubstituted or disubstituted by R$^8$, OH, OR$^8$, COOH, COOA, CN, NO$_2$, NH$_2$, NHCOR$^8$, NHSO$_2$R$^8$, Hal or 1H-tetrazol-5-yl,
Het is a five- or six-membered heteroaromatic radical having 1 to 3 N, O and/or S atoms, which can also be substituted one or more times by A and/ or can be fused to a benzene or pyridine ring, Hal is F, Cl, Br or I and m and n are each 1, 2, 3, 4, 5 or 6, and their salts.

Similar compounds are known from European patent application A2-0 400 974.

The object of the invention was to find novel compounds with valuable properties, especially compounds which can be used for the preparation of drugs.

It has been found that the compounds of formula I and their salts possess very valuable pharmacological properties coupled with a good tolerance. In particular, they exhibit antagonistic properties towards angiotensin II and can therefore be used for the treatment of angiotensin II-dependent hypertension, aldosteronism, cardiac insufficiency and increased intraocular pressure, and of disorders of the central nervous system.

These effects can be determined by conventional in vitro or in vivo methods such as, for example, those described in U.S. Pat. Nos. 4,880,804, 5,036,048 and international patent application 91/14367 and also by A. T. Chiu et al., J. Pharmacol. Exp. Therap. 250, 867–874 (1989), and by P. C. Wong et al., ibid. 252, 719–725 (1990; in vivo, on rats).

The compounds of formula I can be used as pharmaceutical active ingredients in human and veterinary medicine, especially for the prophylaxis and/or therapy of cardiac, circulatory and vascular diseases, in particular of hypertonia, cardiac insufficiency and hyperaldosteronism, and also of hypertrophy and hyperplasia of the blood vessels and of the heart, angina pectoris, cardiac infarcts, stroke, restenoses after angioplasty or by-pass operations, ischemic peripheral vascular diseases increased intraocular pressure, glaucomas, macular degeneration, hyperuricemia, kidney function disorders, e.g. kidney failure, diabetic nephropathy, diabetic retinopathy, psoriasis, of gastrointestinal diseases, diseases of the bladder, lung edemas, chronic bronchitis, angiotensin II-mediated disorders in female reproductive organs, perception disorders, e.g. dementia, amnesia, memory function disorders, anxiety states, depression, epilepsy, of the Parkinson syndrome and/or of bulimia.

The invention relates to the compounds of formula I and their salts and to a process for the preparation of these compounds, characterized in that (a) a compound of formula II

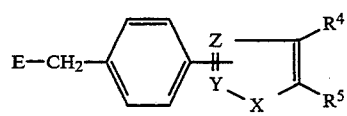

wherein
E is Cl, Br, I, a free OH group or an OH group which has been functionally modified to acquire reactivity, and
X, —Y=Z—, R$^4$ and R$^5$ are as defined above, is reacted with a compound of formula III

wherein
R is as defined above, or
(b) a compound of formula IV

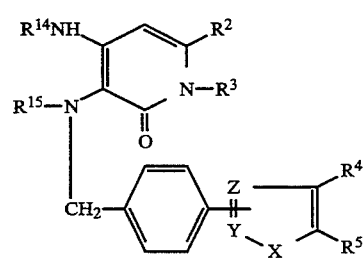

wherein
R$^{14}$ is R$^1$—CO or H,
R$^{15}$ is H (if R$^{14}$ is R$^1$—CO) or R$^1$—CO (if R$^{14}$ is H), and
X, —Y=Z—, R$^1$, R$^2$, R$^3$, R$^4$ and R$^5$ are as defined above, is treated with a cyclizing agent, or
(c) a compound of formula I is freed from one of its functional derivatives by treatment with a solvolyzing or hydrogenolyzing agent, and/or in that one or more radicals R, X and/or —Y=Z— in a compound of formula I are converted to one or more other radicals R, X and/or —Y=Z—, and/or a base or acid of formula I is converted to one of its salts.

Above and below, unless expressly indicated otherwise, the radicals or parameters R, $R^1$ to $R^{15}$, X, —Y=Z—, A, Ar, Het, Hal, m, n and E are as defined in formulae I to IV.

In the above formulae, A has 1–6, preferably 1, 2, 3 or 4 C atoms. A is preferably methyl, or else ethyl, propyl, isopropyl, butyl, isobutyl, sec-butyl or tert butyl, or else pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methoxypropyl or 1,1,2- or 1,2,2-trimethylpropyl. Alkenyl is preferably vinyl, prop-1-enyl, prop-2-enyl or but-1-enyl, further pent-1-enyl or hex-1-enyl. Alkynyl is preferably ethynyl, prop-1-ynyl or prop-2-ynyl, further but-1-ynyl, pent-1-ynyl or hex-1-ynyl. Cycloalkyl is preferably cyclopropyl, further cyclobutyl, cyclopentyl, cyclohexyl or cycloheptyl. The radical OA is preferably methoxy, ethoxy or propoxy. The radical SA is preferably methylthio, ethylthio or propylthio. If several radicals A, or cycloalkyl are present in a compound of the formula I, they can be identical to or different from one another.

Hal is preferably F, Cl or Br, or else I.

R is a radical derived from 3H-imidazo[4,5-c]-pyridine ("3H-IP") or, more precisely, 2-$R^1$-4-oxo-5-$R^3$-6-$R^2$-4,5-dihydro-3H-imidazo[4,5-c]pyridine-3-yl.

Ar is preferably unsubstituted or further, as indicated, monosubstituted phenyl; in detail preferably phenyl, o-, m- or p-tolyl, o-, m- or p-ethylphenyl, o-, m- or p-trifluoromethylphenyl, o-, m- or p-hydroxyphenyl, o-, m- or p-methoxyphenyl, o-, m- or p-ethoxyphenyl, o-, m- or p-difluoromethoxyphenyl, o-, m- or p-trifluoromethoxyphenyl, o-, m- or p-carboxyphenyl, o-, m- or p-methoxycarbonylphenyl, o-, m- or p-ethoxycarbonylphenyl, o-, m- or p-cyanophenyl, o-, m- or p-nitrophenyl, o-, m- or p-aminophenyl, o-, m- or p-acetamidophenyl, o-, m- or p-trifluoroacetamidophenyl, o-, m- or p-methylsulfonamidophenyl, o-, m- or p-trifluoromethylsulfonamidophenyl, o-, m- or p-fluorophenyl, o-, m- or p-chlorophenyl, o-, m- or p-bromophenyl, o-, m- or p-(1H-tetrazol-5-yl)phenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dimethoxyphenyl.

Het is preferably furan-2- or -3-yl, thien-2- or -3-yl, pyrrol-1-, -2- or -3-yl, imidazol-1-, -2-, -4- or -5-yl, pyrazol-1-, -3-, -4- or -5-yl, oxazol-2-, -4- or -5-yl, isoxazol-3-, -4- or -5-yl, thiazol-2-, -4- or -5-yl, isothiazol-3-, -4- or -5-yl, pyridin-2-, -3- or -4-yl or pyrimidin-2-, -4-, -5- or -6-yl, or else preferably 1,2,3-triazol-1-, -4- or -5-yl, 1,2,4- triazol-1-, -3- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3- or -4-yl, 2,1,5-thiadiazol-3- or -4-yl, pyridazin-3- or -4-yl, pyrazinyl, benzofuran-2-, -3-, -4-, -5-, -6- or -7-yl, benzothien-2-, -3-, -4-, -5-, -6- or -7-yl, indol-1-, -2-, -3-, -4-, -5-, -6- or -7-yl, isoindol-1-, -2-, -3-, -4-, -5-, -6- or -7-yl, benzimidazol-1-, -2-, -4- or -5-yl, benzopyrazol-1-, -3-, -4-, -5-, -6- or -7-yl, benzoxazol-2-, -4, -5-, -6- or -7-yl, benzisoxazol-3-, -4-, -5-, -6- or -7-yl, benzthiazol-2-, -4-, -5-, -6- or -7-yl, benzisothiazol-2-, -4-, -5-, -6- or -7-yl, benz-2,1,3- oxadiazol-4-, -5-, -6- or -7-yl, quinol-2-, -3-, -4-, -5-, -6-, -7- or -8-yl, isoquinol-1-, -3-, -4-, -5-, -6-, -7- or -8-yl, cinnolin-3-, -4-, -5- , -6- , -7- or -8-yl, quinazol-2-, -4-, -5-, -6-, -7-, or -8-yl, 1H-imidazo[4,5-b]pyridin-1-, -2-, -5-, -6- or -7-yl, 3H-imidazo[4,5-b]pyridin-2-, -3-, -5-, -6- or -7-yl, 1H-imidazo[4,5-c]pyridin-1-, -2-, -4-, -6- or - 7-yl or 3H-imidazo[4,5-c]pyridin-2-, -3-, -4-, -6- or -7-yl.

The term "Het" also includes the homologous radicals in which the heteroaromatic ring is substituted by one or more, preferably 1 or 2 groups A, preferably methyl and/or ethyl groups, for example 3-, 4- or 5-methylfuran-2-yl, 2-, 4- or 5-methylfuran-3-yl, 2,4-dimethylfuran-3-yl, 3-, 4- or 5-methylthien-2-yl, 3-methyl-5-tert-butylthien-2-yl, 2-, 4- or 5-methylthien-3-yl, 2- or 3-methylpyrrol-1-yl, 1-, 3-, 4- or 5-methylpyrrol-2-yl, 3,5-dimethyl-4-ethylpyrrol-2-yl, 2-, 4- or 5-methylimidazol-1-yl, 4-methylpyrazol-5-yl, 4- or 5-methylisoxazol-3-yl, 3- or 5-methylisoxazol-4-yl, 3- or 4-methylisoxazol-5-yl, 3,4-dimethylisoxazol-5-yl, 4- or 5-methylthiazol-2-yl, 4- or 5-ethylthiazol-2-yl, 2- or 5-methylthiazol-4-yl, 2- or 4-methylthiazol-5-yl, 2,4-dimethylthiazol-5-yl, 3-, 4-, 5- or 6-methylpyridin-2-yl, 2-, 4-, 5- or 6-methylpyridin-3-yl, 2- or 3-methyl-pyridin-4-yl, 4-methylpyrimidin-2-yl, 4,5-dimethyl-pyrimidin-2-yl, 2-, 5- or 6-methylpyrimidin-4-yl, 2,6-dimethylpyrimidin-4-yl, 3-, 4-, 5-, 6- or 7-methyl-benzofuran-2-yl, 2-ethylbenzofuran-3-yl, 3-, 4-, 5-, 6- or 7-methyl-benzothien-2-yl, 3-ethylbenzothien-2-yl, 1-, 2-, 4-, 5-, 6- or 7-methylindol-3-yl, 1-methyl-benzimidazol-5- or -6-yl or 1-ethylbenzimidazol-5- or -6-yl.

Preferably, the radical $R^1$ is linear and is A, alkenyl or cycloalkyl each having 3–6 C atoms, in particular butyl, or else propyl, pentyl, hexyl, allyl, prop-1-enyl, cyclopropyl, or else but-1-enyl, pent-1-enyl, hex-1-enyl, prop-1-ynyl, but-1-ynyl, pent-1-ynyl, hex-1-ynyl, cyclobutyl or cyclopentyl.

The radical $R^2$ is preferably H, or else F, Cl, Br or I.

The radical $R^3$ is preferably —$C_nH_{2n}R^9$ (in detail preferably —$CH_2R^9$).

The radicals $R^4$ and $R^5$ are preferably identical and are preferably H, or else F, Cl, Br or I.

The radical $R^6$ is preferably H or —$CH_2$—$R^{10}$.

The radical $R^7$ is preferably CN or 1H-5-tetrazolyl.

Preferably, the radical $R^8$ contains 1, 2 or 3 C atoms and is preferably methyl, ethyl, trifluoromethyl, pentafluoroethyl, 2,2,2-trifluoroethyl or 3,3,3-trifluoropropyl. If a compound of formula I contains two radicals $R^8$, these can be identical to or different from one another.

The radical $R^9$ is preferably COOH; COOA, in particular $COOCH_3$ or $COOC_2H_5$; CONHA; in particular $CONHCH_3$ or $CONHC_2H_5$; CON(A)$_2$, in particular $CON(CH_3)_2$ or $CON(C_2H_5)_2$; CONHAr, in particular $CONHC_6H_5$ or CONH- (2,6-dimethyl-phenyl); COA, in particular $COCH_3$, $COC_2H_5$, $COC_3H_7$, $COCH(CH_3)_2$ or $COC(CH_3)_3$; COAr, in particular $COC_6H_5$, CO-(2-$CH_3O$—$C_6H_4$) or CO- (2-$CH_3$—$C_6H_4$).

$R^{10}$ is preferably COOH or COOA.

$R^{11}$, $R^{12}$ and $R^{13}$ are each preferably H, $CH_3$ or $C_2H_5$.

m is preferably 1, furthermore preferably 2.

n is preferably 1, furthermore preferably 2, 3 or 4.

The group —$C_mH_{2m}$— is in particular —$(CH_2)_m$—, preferably —$CH_2$—. The group —$C_nH_{2n}$— is in particular —$(CH_2)_n$—, preferably —$CH_2$—.

The radical X is preferably S, furthermore preferably $NR^6$. The group —Y=Z— is preferably

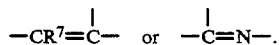

The compounds of formula I can possess one or more chiral centres and can therefore exist in different forms (optically active or optically inactive). Formula I includes all these forms.

Accordingly the invention relates especially to those compounds of formula I in which at least one of said radicals has one of the preferred meanings indicated above. Some preferred groups of compounds can be expressed by the following partial formulae Ia to Ih, which correspond to formula I and wherein the radicals not described more precisely are as defined in formula I, except that the group

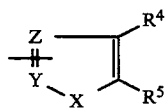

in Ia is 2-cyano-3-thienyl;
in Ib is 2-(1H-5-tetrazolyl)-3-thienyl;
in Ic is 1-cyanomethyl-2-imidazolyl;
in Id is 1-carboxymethyl-2-imidazolyl;
in Ie is 1-(1H-5-tetrazolyl)-2-imidazolyl;
in If is 1-cyanomethyl-4,5-dichloro-2-imidazolyl;
in Ig is 1-carboxymethyl-4,5-dichloro-2-imidazolyl;
in Ih is 1-(1H-5-tetrazolyl)-4,5-dichloro-2-imidazolyl.

Compounds of formulae Ia and Ib are particularly preferred.

The following are also preferred: compounds of formulae Ii and Iai to Ihi, which correspond to the compounds of formulae I and Ia to Ih, except that $R^1$ is A or cycloalkyl having 3–7 C atoms, in particular butyl; compounds of formulae Ij, Iaj to Iij and Iaij to Ihij, which correspond to formulae I, Ia to Ii and Iai to Ihi, except that $R^2$ is H; compounds of formulae Ik and Iak to Ihk, which correspond to formulae I and Ia to Ih, except that in addition $R^1$ is butyl and $R^2$ is H.

Other preferred groups of compounds have formula I and the other formulae given above, except that the radical $R^3$ is defined as follows:

(a) H,
(b) $R^8$,
(c) A,
(d) $-C_nH_{2n}-R^9$,
(e) $-CH^2-R^9$,
(f) $-COOR^{12}$,
(g) $-CONR^{12}R^{13}$,
(h) $-COA$,
(i) $-NR^{12}R^{13}$,
(j) $-(C_3-C_7-cycloalkyl)$,
(k) $-CH_2-Ar$,
(l) $-CH_2-Het$,
(m) $-CH_2-COAr$,
(n) $-CH_2-COHet$,
(o) unsubstituted benzyl or benzyl which is substituted (preferably in the 2-position) by F, Cl, $COOR^{12}$, $NO_2$, $NH_2$, $N(A)_2$ or NHCOA,
(p) A or $-CH_2-R^9$, where $R^9$ is COOH, COOA, CON $(A)_2$, $CONHC_6H_5$, CONH (2,6-di-$CH_3-C_6H_3$), COA, $C_6H_5$, a benzyl group which is monosubstituted in the 2-position by F, Cl, COOH, COOA, $NO_2$, $NH_2$, $N(A)_2$ or NHCO, or benzoyl or 2-methoxybenzoyl,
(q) 2-(COOA)-benzyl.

The compounds of formula I and also the starting materials for their preparation are moreover prepared by methods known per se, such as those described in the literature (for example in the standard works like Houben-Weyl, Methoden der organischen Chemie (Methods of Organic Chemistry), Georg-Thieme-Verlag, Stuttgart, but especially in European patent application A2-0 430 709 and U.S. Pat. No.4,880,804), under conditions which are known and suitable for said reactions, it also being possible to make use of variants known per se, which are not mentioned in greater detail here.

If desired, the starting materials can also be formed in situ, so that they are not isolated from the reaction mixture but immediately reacted further to give the compounds of formula I.

The compounds of formula I can preferably be obtained by reacting compounds of formula II with compounds of formula III.

In the compounds of formula II, E is preferably Cl, Br, I or an OH group which has been functionally modified to acquire reactivity, such as alkylsulfonyloxy having 1–6 C atoms (preferably methylsulfonyloxy) or arylsulfonyloxy having 6–10 C atoms (preferably phenyl- or p-tolyl-sulfonyloxy).

The reaction of II with III is conveniently carried out by first converting III to a salt by treatment with a base, for example with an alkali metal alcoholate such as $CH_3ONa$ or potassium tert-butylate in an alcohol such as methanol or tert-butanol, or with an alkali metal hydride such as NaH, or with an alkali metal alcoholate in dimethylformamide (DMF), and then reacting said salt with II in an inert solvent, for example an amide such as DMF or dimethylacetamide, or a sulfoxide such as dimethyl sulfoxide (DMSO), conveniently at temperatures of between $-20°$ and $100°$, preferably of between $10°$ and $30°$. Other suitable bases are alkali metal hydrogen carbonates such as $NaHCO_3$ or $KHCO_3$.

The compounds of formula I can also be obtained by the cyclization of compounds of formula IV. This cyclization is conveniently carried out by heating with polyphosphoric acid, acetic acid or diglyme to temperatures of between about $80°$ and $180°$, preferably of between $120°$ and $160°$.

It is also possible to free a compound of formula I from one of its functional derivatives by solvolysis (for example hydrolysis) or hydrogenolysis.

Thus it is possible, using one of the methods indicated, to prepare a compound which has formula I but in which a tetrazol-5-yl group is replaced with a 1H(or 2H)-tetrazol-5-yl group functionally modified in the 1-position (or 2-position) (protected by a protecting group). Examples of suitable protecting groups are: triphenylmethyl, which can be cleaved with HCl or formic acid in an inert solvent or solvent mixture, for example dioxane or ether/methylene chloride/methanol; 2-cyanoethyl, which can be cleaved with NaOH in water/THF; and p-nitrobenzyl, which can be cleaved with $H_2$/Raney nickel in ethanol (compare European patent application A2-0 291 969).

Some of the starting materials, especially those of formula II, are known. If they are not known, they can be prepared by known methods analogously to known substances.

Compounds of formula III can be obtained for example by reacting carboxylic acids of the formula R¹—COOH with compounds of formula V

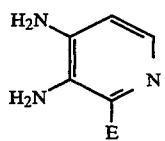

in the presence of polyphosphoric acid; the group E (preferably Cl) is hydrolyzed in the process and compounds of formula III where $R^3=H$ are formed initially; these can then be reacted, if desired, with compounds of formula E—$R^3$ (wherein $R^3$ differs from H).

Compounds of formula IV can be obtained for example by reacting compounds of formula. VI

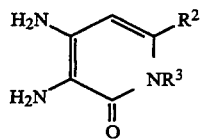

wherein, however, one of the amino groups is protected by an amino-protecting group (for example benzyl, A—O—CO— or benzyloxycarbonyl), with compounds of formula II and subsequently cleaving the protecting group and reacting the products with acids of the formula R¹—COOH or functional derivatives thereof; they are not normally isolated, but are formed in situ in the last-mentioned reaction.

It is also possible to convert one compound of formula I to another compound of formula I by converting one or more of the radicals R, X and/or —Y=Z— to other radicals R, X and/or —Y=Z—, for example by reducing nitro groups to amino groups (for example by hydrogenation on Raney nickel or Pd on charcoal in an inert solvent such as methanol or ethanol), and/or functionally modifying free amino and/or hydroxyl groups, and/or freeing functionally modified amino and/or hydroxyl groups by solvolysis or hydrogenolysis, and/or hydrolyzing nitrile groups to COOH groups, or converting nitrile groups to tetrazolyl groups with hydrazoic acid derivatives, for example sodium azide in N-methylpyrrolidone or trimethyltin azide in toluene.

Thus, for example, free amino groups can be acylated in a conventional manner with an acid chloride or anhydride, or alkylated with an unsubstituted or substituted alkyl halide, conveniently in an inert solvent such as methylene chloride or THF, and/or in the presence of a base such as triethylamine or pyridine, at temperatures of between −60° and +30°.

Conversely, a functionally modified amino and/or hydroxyl group in a compound of formula I can be freed by solvolysis or hydrogenolysis using conventional methods. Thus, for example, an NHCOR⁸ or COOA group can be converted to the corresponding NH₂ or HOOC group. COOA groups can be saponified for example with NaOH or KOH in water, water/THF or water/dioxane, at temperatures of between 0° and 100°.

The reaction of nitriles of formula I (for example those in which $R^7$ or $R^{10}$=CN) with hydrazoic acid derivatives leads to tetrazoles of formula I (for example in which $R^7$ or $R^{10}$=1H-tetrazol-5-yl). It is preferable to use trialkyltin azides such as trimethyltin azide, in an inert solvent, for example an aromatic hydrocarbon such as toluene, at temperatures of between 20° and 150°, preferably of between 80° and 140°, or sodium azide in N-methylpyrrolidone at temperatures of between about 100° and 200°. The trialkyl tin group is then eliminated, either by treating with hydrochloric acid, for example in dioxane, or with alkali, for example in ethanol/water, or with formic acid, for example in methanol, or by chromatography on a silica gel column, for example using ethyl acetate/methanol.

A base of formula I can be converted with an acid to the corresponding acid addition salt, for example by reaction of equivalent amounts of the base and of the acid in an inert solvent such as ethanol and subsequent evaporation. Possible acids for this reaction are especially those which yield physiologically acceptable salts. Thus it is possible to use inorganic acids, for example sulfuric acid, nitric acid, hydrohalic acids such as hydrochloric acid or hydrobromic acid, phosphorus acids such as orthophosphoric acid, and sulfamic acid, as well as organic acids, especially aliphatic, alicyclic, araliphatic, aromatic or heterocyclic monobasic or polybasic carboxylic, sulphonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulphonic acid, ethanedisulfonic acid, 2-hydroxyethanesulfonic acid, benzenesulfonic acid, p-toluenesulfonic acid, naphthalene-monosulfonic and -disulfonic acids and laurylsulfuric acid. Salts with physiologically unacceptable acids, for example picrates, can be used for isolating and/or purifying the compounds of formula I.

On the other hand, compounds of formula I containing COOH and/or tetrazolyl groups can be converted with bases (for example sodium or potassium hydroxide or carbonate) to the corresponding metal salts, especially alkali metal or alkaline earth metal salts, or to the corresponding ammonium salts. The potassium salts of the tetrazolyl derivatives are particularly preferred.

The novel compounds of formula I and their physiologically acceptable salts can be used for the manufacture of pharmaceutical preparations by incorporation into a suitable dosage form together with at least one excipient or adjunct and, if desired, together with one or more other active ingredients. The resulting formulations can be used as drugs in human or veterinary medicine. Possible excipients are organic or inorganic substances which are suitable for enteral (for example oral or rectal) or parenteral administration or for administration in the form of an inhalation spray, and which do not react with the novel compounds, examples being water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; lacquered tablets and capsules with coatings or shells resistant to gastric juices are of special interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant mixture (for example fluorochlorohydrocarbons). It is convenient here to use the active ingredient in micronized form, it being possible for one or more additional physiologically compatible solvents, for example ethanol, to be present. Inhalation solutions can be administered with the aid of conventional inhalers. The novel compounds can be lyophilized and the resulting lyophilisates used for example for the manufacture of injectable preparations. The indicated formulations can be sterilized and/or can contain adjuncts such as preservatives, stabilizers and/or wetting agents, emulsifiers, salts for influencing the osmotic pressure, buffer substances and colours and/or flavourings. If desired, they can also contain one or more other active ingredients, for example one or more vitamins, diuretics or antiphlogistics.

The substances according to the invention are normally administered analogously to other known, commercially available preparations, but in particular analogously to the compounds described in U.S. Pat. No. 4,880,804, preferably in doses of between about 1 mg and 1 g, especially of between 50 and 500 mg per dosage unit. The daily dose is preferably between about 0.1 and 50 mg/kg, especially between 1 and 10 mg/kg of body weight. However, the particular dose for each individual patient depends on a very wide variety of factors, for example on the efficacy of the particular compound used, age, body weight, general state of health, sex, diet, time and mode of administration, rate of excretion, drug combination and severity of the particular disease to which the therapy is applied. Oral administration is preferred.

Above and below, all temperatures are given in ° C. In the following Examples, "conventional working-up" means: Water is added if necessary, the pH is adjusted to between 2 and 10 if necessary, depending on the constitution of the end product, extraction is carried out with ethyl acetate or methylene chloride and the organic phase is separated off, dried over sodium sulfate, evaporated and purified by chromatography on silica gel and/or by crystallization.

IP=imidazo[4,5-c]pyridine, IPs=imidazo[4,5-c]pyridines. the residue is dissolved in 20 ml of DMF, and a solution Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 42 36 026.9, filed Oct. 24, 1992, are hereby incorporated by reference.

EXAMPLES

Example 1

A solution of 0.23 g of Na in 20 ml of methanol is added dropwise over 15 minutes to a solution of 1.91 g of 2-butyl-4,5-dihydro-4-oxo-1(or 3)H-IP ("IIIa"; obtainable by condensation of valeric acid with 3,4-diamino-2-chloropyridine in the presence of polyphosphoric acid) in 75 ml of methanol. The mixture is stirred for a further 30 minutes at 20° and evaporated, the residue is dissolved in 20 ml of DMF, and a solution of 2.78 g of 2-cyano-3-(4-bromomethylphenyl) thiophene ("IIA"; m.p. 58° obtainable by reaction of 2-cyano-3-bromothiophene with 4-(dimethyl (1,1,2-trimethylpropyl)silyloxymethyl)phenylboronic acid to give 2-cyano-3-(4-(dimethyl(1,1,2-trimethylpropyl)silyloxymethyl)phenyl)thiophene and reaction with triphenylphosphine bromide] is added dropwise with stirring at 0° in 10 ml of DMF. The mixture is stirred for 16 hours at 20° and evaporated, worked up in the conventional manner and chromatographed on silica gel to give 2-butyl-3-(4-(2-cyano- 3-thienyl)benzyl)-4,5-dihydro-4-oxo-3H-IP, m.p. 219°.

The following are obtained analogously from IIIa:
with 2-methoxycarbonyl-3-(4-bromomethylphenyl) thiophene (obtainable from methyl 3-bromothiophene-2-carboxylate via 2-methoxycarbonyl-3-(4-(dimethyl (1,1,2-trimethylpropyl)silyloxymethyl)phenyl)thiophene analogously to IIa):
2-butyl-3-(4-(2-methoxycarbonyl-3-thienyl) benzyl)-4,5-dihydro-4-oxo-3H-IP;
with 1-cyanomethyl-2-(4-bromomethylphenyl)imidazole (obtainable from 1-cyanomethyl-2-bromoimidazole analogously to IIa):
2-butyl-3-(4-(1-cyanomethyl-2-imidazolyl)benzyl)-4,5-dihydro-4-oxo-3H-IP;
with 1-cyanomethyl-2-(4-bromomethylphenyl)-4,5-dichloro imidazole (obtainable from 1-cyanomethyl-2-bromo-4,5-dichloroimidazole analogously to IIa):
2-butyl-3-(4-(1-cyanomethyl-4,5-dichloro-2imidazolyl)benzyl)-4,5-dihydro-4-oxo-3H-IP;
with 1-ethoxycarbonylmethyl-2-(4-bromomethylphenyl) imidazole (obtainable from 1-ethoxycarbonylmethyl-2-bromo-imidazole analogously to IIa):
2-butyl-3-(4-(1-ethoxycarbonylmethyl-2-imidazolyl)-benzyl)-4,5-dihydro-4-oxo-3H-IP;
with 1-ethoxycarbonylmethyl-2-(4-bromomethylphenyl)-4,5-dichloroimidazole (m.p. 99°–100°; obtainable from 1-ethoxycarbonylmethyl-2-bromo-4,5-dichloroimidazole analogously to IIa):
2-butyl-3-(4-(1-ethoxycarbonylmethyl-4,5-dichloro-2-imidazolyl)benzyl)-4,5-dihydro-4-oxo-3H-IP.

The following are obtained analogously from IIa:
with 2-propyl-4,5-dihydro-4-oxo-1(or 3)H-IP:
2-propyl-3-(4-(2-cyano-3-thienyl)benzyl)-4,5-dihydro-4-oxo-3H-IP;
with 2-cyclopropyl-4,5-dihydro-4-oxo-1(or 3)H-IP:
2-cyclopropyl-3-(4-(2-cyano-3-thienyl)benzyl)-4,5-dihydro-4-oxo-3H-IP.

Example 2

A mixture of 1.02 g of valeric acid, 4.50 g of 4-amino-1,2-dihydro-2-oxo-3-(4-(2-(1H-5-tetrazolyl)-3-thienyl)-benzylamino)-1-(N,N-dimethylcarbamoylmethyl)pyridine [obtainable by reaction of 3-amino-4-benzylamino-1,2-dihydro-2-oxo-1-(N,N-dimethylcarbamoylmethyl)-pyridin with IIa to give 4-benzylamino-3-oxo-1-(N,N-dimethylcarbamoylmethyl)pyridine, reaction with trimethyltin azide to give 4-benzylamino-1,2-dihydro-2-oxo-3-(4-(2-(1H-5-tetrazolyl)-3-thienyl)benzylamino)-1-(N,N-dimethylcarbamoylmethyl)pyridine and hydrogenolytic removal of the benzyl group] and 50 g of polyphosphoric acid is heated for 5 hours at 140°. 4-Amino-1,2-dihydro-2-oxo-3-(N-4-(2-(1H-5-tetrazolyl)-3-thienyl)benzyl-N-valerylamino)-1-(N,N-dimethylcarbamoylmethyl)pyridine and 1,2-dihydro-2-oxo-3-(4-(2-

(1H-5-tetrazolyl)-3-thienylbenzylamino)-1-(N,N-dimethylcarbamoylmethyl)-4-valerylaminopyridine are formed in situ as intermediates. The mixture is cooled, poured onto ice, rendered alkaline with sodium hydroxide solution and worked up in the conventional manner, and gives 2-butyl-3-(4-(2-(1H-5-tetrazolyl)-3-thienyl)-benzyl-4,5-dihydro-4-oxo-5-(N,N-dimethylcarbamoylmethyl)-3H-IP.

Example 3

1 g of 2-butyl-3-(4-(2-(2-triphenylmethyl-2H-5tetrazolyl)-3-thienyl)benzyl)-4,5-dihydro-4-oxo-5-(2-methoxycarbonylbenzyl)-3H-IP (IIIb; obtainable by reaction of IIIa with 2-triphenylmethyl-5-(3-(4-bromomethylphenyl-3-thienyl)-2H-tetrazole to give 2-butyl-3-(4-(2-(2-triphenylmethyl-2H-5-tetrazolyl)-3-thienyl)benzyl)-4,5-dihydro-4-oxo-3H-IP and reaction with methyl 2-bromomethylbenzoate analogously to Example 4) is dissolved in 60 ml of 4N HCl in dioxane and stirred for 16 hours at 20°. The mixture is evaporated, and the residue is worked up in the conventional manner and gives 2-butyl-3-(4-(2-(1H-5-tetrazolyl)-3-thienyl)benzyl)-4,5-dihydro-4-oxo-5-(2-methoxycarbonylbenzyl)-3H-IP, hydrate, m.p. 186° (dec.).

Analogously, reaction of the 2-butyl-3-(4-(2-(2-triphenylmethyl-2H-5-tetrazolyl)-3-thienyl)benzyl-)-4,5-dihydro-4-oxo-5-R3-3H-Ips below (obtainable from IIIb and the halides given in Example 4(a) analogously to Example 4(a)):
-5-methyl-
-5-isopropyl-
-5-butyl-
-5-trifluoromethyl-
-5-carboxymethyl-
-5-methoxycarbonylmethyl-
-5-ethoxycarbonylmethyl-
-5-phenoxycarbonylmethyl-
-5-carbamoylmethyl-
-5-(N-methylcarbamoylmethyl)-
-5-(N,N-dimethylcarbamoylmethyl)-
-5-(N,N-diethylcarbamoylmethyl)-
-5-(N-phenylcarbamoylmethyl)-
-5-(N-(2,6-dimethylphenyl)carbamoylmethyl)-
-5-(N-methyl-N-phenylcarbamoylmethyl)-
-5-(2-oxopropyl)-
-5-(2-oxo-3,3-dimethylbutyl)-
-5-(2-dimethylaminoethyl)-
-5-(2-anilinoethyl)-
-5-cyclopropylmethyl-
-5-cyclobutylmethyl-
-5-cyclopentylmethyl-
-5-cyclohexylmethyl-
-5-benzyl-
-5-(2-fluorobenzyl)-
-5-(2-chlorobenzyl)-
-5-(2-carboxybenzyl)-
-5-(2-ethoxycarbonylbenzyl)-
-5-(2-nitrobenzyl)-
-5-(2-dimethylaminobenzyl)-
-5-(2-acetamidobenzyl)-
-5-(4-methoxybenzyl)-
-5-(2-thienylmethyl)-
-5-phenacyl-
-5-(2-methoxyphenacyl)-
-5-(2-oxo-2-(2-pyridyl)ethyl)-
with HCl in dioxane gives the 2-butyl-3-(4-(2-(1H-5-tetrazolyl)-3-thienyl)benzyl)-4,5-dihydro-4-oxo-5-R3-3H-IPs given in Example 4(b).

Example 4

(a) A solution of 3.88 g of 2-butyl-3-(4-(2-cyano-3-thienyl)benzyl)-4,5-dihydro-4-oxo-3H-IP in 35 ml of DMF is treated with 1.25 g of K tert-butoxide with stirring at 20°. After stirring for 45 minutes, a solution of 2.63 g of methyl 2-bromomethylbenzoate in 25 ml of DMF is added dropwise. The mixture is stirred for a further 16 hours at 20°, worked up in the conventional manner and gives 2-butyl-3-(4-(2-cyano-3-thienyl)benzyl)-4,5-dihydro-4-oxo-5-(2-methoxycarbonylbenzyl)-3H-IP, m.p. 121°. The 2-butyl-3-(4-(2-cyano-3-thienyl)benzyl)-4-5-dihydro-4-oxo-5-R3-3H-IPs below are obtained analogously:

| | |
|---|---|
| with methyl iodide: | -5-methyl- |
| with isopropyl bromide: | -5-isopropyl- |
| with butyl bromide: | -5-butyl- |
| with trifluoromethyl iodide: | -5-trifluoromethyl- |
| with bromoacetic acid: | -5-carboxymethyl- |
| with methyl bromoacetate: | -5-methoxycarbonylmethyl- |
| with ethyl bromoacetate: | -5-ethoxycarbonylmethyl- |
| with phenyl bromoacetate: | -5-phenoxycarbonylmethyl- |
| with bromoacetamide: | -5-carbamoylmethyl-,m.p. 162–164° |
| with N-methylbromoacetamide: | -5-(N-methylcarbamoylmethyl)- |
| with N,N-dimethylchloroacetamide: | -5-(N,N-dimethylcarbamoylmethyl)-,m.p.113–115° |
| with N,N-diethylchloroacetamide: | -5-(N,N-diethylcarbamoylmethyl)-,m.p. 126–128° |
| with chloroacetanilide: | -5-(N-phenylcarbamoylmethyl)- |
| with chloroacetic acid(2,6-dimethylanilide): | -5-(N-(2,6-dimethylphenyl)carbamoylmethyl)- |
| with N-methyl-N-phenylchloroacetamide: | -5-(N-methyl-N-phenylcarbamoylmethyl) - |
| with bromoacetone: | -5-(2-oxopropyl)- |
| with 1-bromo-3,3-dimethyl-2-butanone: | -5-2-oxo-3,3 - dimethylbutyl)- |
| with 2-dimethylaminoethyl chloride: | -5-(2-dimethylaminoethyl)- |
| with 2-anilinoethyl chloride: | -5-(2-anilinoethyl)- |
| with cyclopropylmethyl bromide: | -5-cyclopropylmethyl- |
| with cyclobutylmethyl chloride: | -5-cyclobutylmethyl- |
| with cyclopentylmethyl chloride: | -5-cyclopentylmethyl- |
| with cyclohexylmethyl chloride: | -5-cyclohexylmethyl- |
| with benzyl bromide: | -5-benzyl- |
| with 2-fluorobenzyl bromide: | -5-(2-fluorobenzyl)- |
| with 2-chlorobenzyl bromide: | -5-(2-chlorobenzyl)- |
| with 2-bromomethylbenzoic acid | -5-(2-carboxybenzyl)- |
| with ethyl 2-bromomethylbenzoate: | -5-(2-ethoxycarbonylbenzyl)- |
| with 2-nitrobenzyl chloride: | -5-(2-nitrobenzyl)- |
| with 2-dimethylaminobenzyl chloride: | -5-(2-dimethylaminobenzyl)- |
| with 2-acetamidobenzyl chloride: | -5-(2-acetamidobenzyl)- |
| with 4-methoxybenzyl chloride: | -5-(4-methoxybenzyl)- |
| with 2-thienylmethyl chloride: | -5-(2-thienylmethyl)- |
| with phenacyl bromide: | -5-phenacyl- |
| with 2-methoxyphenacyl chloride: | -5-(2-methoxyphenacyl)- |
| with 2-oxo-2-(2-pyridyl)ethyl chloride: | -5-(2-oxo-2-(2-pyridyl)-ethyl)-. |

(b) A mixture of 5.37 g of the compound obtained as in (a), 20.6 g of trimethyltin azide and 200 ml of toluene is boiled for 24 hours and then evaporated. The residue is taken up in 100 ml of methanolic HCl, stirred for 2 hours at 20° and worked up in the conventional manner (saturated NaCl solution/dichloromethane). Chromatography (ethyl acetate/hexane 80:20) gives 2-butyl-3-(4-(2-(1H-5-tetrazolyl)-3-thienyl)benzyl)-4,5-dihydro-4-oxo-5-(2-methoxycarbonylbenzyl)-3H-IP, hydrate, m.p. 186° (dec.).

The 2-butyl-3-(4-(2-(1H-5-tetrazolyl)-3thienyl)benzyl)-4,5-dihydro-4-oxo-5-$R^3$-3H-IPs. Below are obtained analogously from the 2-cyano-3-thienyl compounds given in (a):
-5-methyl-
-5-isopropyl-
-5-butyl-
-5-trifluoromethyl-
-5-carboxymethyl-
-5-methoxycarbonylmethyl-
-5-ethoxycarbonylmethyl-
-5-phenoxycarbonylmethyl-
-5-carbamoylmethyl-, m.p.261°–262°; K salt, m.p. 292°–293°
-5-(N-methylcarbamoylmethyl) -
-5-(N, N-dimethylcarbamoylmethyl)-, m.p.216°; K salt, hydrate, m.p. 275°
-5-(N, N-diethylcarbamoylmethyl)-, m.p.95°–96°; K salt, m.p.284°–285°
-5-(N-phenylcarbamoylmethyl)-
-5-(N-(2,6-dimethylphenyl)carbamoylmethyl)-
-5-(N-methyl-N-phenylcarbamoylmethyl)-
-5-(2-oxopropyl)-
-5-(2-oxo-3,3-dimethylbutyl)-
-5-(2-dimethylaminoethyl)-
-5-(2-anilinoethyl)-
-5-cyclopropylmethyl-
-5-cyclobutylmethyl-
-5-cyclopentylmethyl-
-5-cyclohexylmethyl-
-5-benzyl-
-5-(2-fluorobenzyl)-
-5-(2-chlorobenzyl)-
-5-(2-carboxybenzyl)-
-5-(2-ethoxycarbonylbenzyl)-
-5-(2-nitrobenzyl)-
-5-(2-dimethylaminobenzyl)-
-5-(2-acetamidobenzyl)-
-5-(4-methoxybenzyl)-
-5-(2-thienylmethyl)-
-5-phenacyl-
-5-(2-methoxyphenacyl)-
-5-(2-oxo-2-(2-pyridyl)ethyl)-

Example 5

(a) Analogously to Example 4(a), 2-butyl-3-(4-(1-cyanomethyl-2-imidazolyl)benzyl)-4,5-dihydro-4-oxo-3H-IP and methyl 2-bromomethylbenzoate give 2-butyl-3-(4-(1-cyanomethyl-2-imidazolyl)-benzyl)-4,5-dihydro-4-oxo-5-(2-methoxycarbonylbenzyl)-3H-IP.

The 2-butyl-3-(4-(1-cyanomethyl-2-imidazolyl)benzyl)-4,5-dihydro-4-oxo-5-$R^3$-3H-IPs below are obtained analogously:

| | |
|---|---|
| with methyl iodide: | -5-methyl- |

-continued

| | |
|---|---|
| with isopropyl bromide: | -5-isopropyl- |
| with butyl bromide: | -5-butyl- |
| with trifluoromethyl iodide: | -5-trifluoromethyl- |
| with bromoacetic acid: | -5-carboxymethyl- |
| with methyl bromoacetate: | -5-methoxycarbonylmethyl- |
| with ethyl bromoacetate: | -5-ethoxycarbonylmethyl- |
| with phenyl bromoacetate: | -5-phenoxycarbonylmethyl- |
| with bromoacetamide: | -5-carbamoylmethyl- |
| with N-methylbromoacetamide: | -5-(N-methylcarbamoylmethyl)- |
| with N,N-dimethylchloroacetamide: | -5-(N,N-dimethylcarbamoylmethyl)- |
| with N,N-diethylchloroacetamide: | -5-(N,N-diethylcarbamoylmethyl)- |
| with chloroacetanilide: | -5-(N-phenylcarbamoyl-methyl)- |
| with chloroacetic acid(2,6-dimethylanilide): | -5-(N-(2,6-dimethylphenyl)carbamoylmethyl)- |
| with N-methyl-N-phenyl-chloroacetamide: | -5-(N-methyl-N-phenylcarbamoylmethyl)- |
| with bromoacetone: | -5-(2-oxopropyl)- |
| with 1-bromo-3,3-dimethyl-2-butanone: | -5-2-oxo-3,3-dimethylbutyl)- |
| with 2-dimethylaminoethyl chloride: | -5-(2-dimethylaminoethyl)- |
| with 2-anilinoethyl chloride: | -5-(2-anilinoethyl)- |
| with cyclopropylmethyl bromide: | -5-cyclopropylmethyl- |
| with cyclobutylmethyl chloride: | -5-cyclobutylmethyl- |
| with cyclopentylmethyl chloride: | -5-cyclopentylmethyl- |
| with cyclohexylmethyl chloride: | -5-cyclohexylmethyl- |
| with benzyl bromide: | -5-benzyl- |
| with 2-fluorobenzyl bromide: | -5-(2-fluorobenzyl)- |
| with 2-chlorobenzyl bromide: | -5-(2-chlorobenzyl)- |
| with 2-bromomethylbenzoic acid | -5-(2-carboxybenzyl)- |
| with ethyl 2-bromomethyl-benzoate: | -5-(2-ethoxycarbonylbenzyl)- |
| with 2-nitrobenzyl chloride: | -5-(2-nitrobenzyl)- |
| with 2-dimethylaminobenzyl chloride: | -5-(2-dimethylaminobenzyl)- |
| with 2-acetamidobenzyl chloride: | -5-(2-acetamidobenzyl)- |
| with 4-methoxybenzyl chloride: | -5-(4-methoxybenzyl)- |
| with 2-thienylmethyl chloride: | -5-(2-thienylmethyl)- |
| with phenacyl bromide: | -5-phenacyl- |
| with 2-methoxyphenacyl chloride: | -5-(2-methoxyphenacyl)- |
| with 2-oxo-2-(2-pyridyl)ethyl chloride: | -5-(2-oxo-2-(2-pyridyl)ethyl)-. |

(b) Analogously to Example 4(b), the 2-butyl-3-(4-(1-(1H-5-tetrazolylmethyl)-2-imidazolyl)benzyl)-4,5-dihydro-4-oxo-5-$R^3$-3H-IPs below are obtained from the 1-cyano-methyl-2-imidazolyl compounds given in (a) using trimethyltin azide:
-5-methyl-
-5-isopropyl-
-5-butyl-
-5-trifluoromethyl-
-5-carboxymethyl-
-5-methoxycarbonylmethyl-
-5-ethoxycarbonylmethyl-
-5-phenoxycarbonylmethyl-
-5-carbamoylmethyl-
-5-(N-methylcarbamoylmethyl)-
-5-(N,N-dimethylcarbamoylmethyl)-
-5-(N,N-diethylcarbamoylmethyl)-
-5-(N-phenylcarbamoylmethyl)-
-5-(N-(2,6-dimethylphenyl)carbamoylmethyl)-
-5-(N-methyl-N-phenylcarbamoylmethyl)-
-5-(2-oxopropyl)-

-5-(2-oxo-3,3-dimethylbutyl)-
-5-(2-dimethylaminoethyl)-
-5-(2-anilinoethyl)-
-5-cyclopropylmethyl-
-5-cyclobutylmethyl-
-5-cyclopentylmethyl-
-5-cyclohexylmethyl-
-5-benzyl-
-5-(2-fluorobenzyl)-
-5-(2-chlorobenzyl)-
-5-(2-carboxybenzyl)-
-5-(2-ethoxycarbonylbenzyl)-
-5-(2-nitrobenzyl)-
-5-(2-dimethylaminobenzyl)-
-5-(2-acetamidobenzyl)-
-5-(4-methoxybenzyl)-
-5-(2-thienylmethyl)-
-5-phenacyl-
-5-(2-methoxyphenacyl)-
-5-(2-oxo-2-(2-pyridyl)ethyl)-

Example 6

(a) Analogously to Example 4(a), 2-butyl-3-(4-(1-cyanomethyl-4,5-dichloro-2-imidazolyl)benzyl)-4,5-dihydro-4-oxo-5-(2-methoxycarbonylbenzyl)-3H-IP is obtained from 2-butyl-3-(4-(1-cyanomethyl-4,5-dichloro-2-imidazolyl)benzyl)-4,5-dihydro-4-oxo-3H-IP and methyl 2bromomethylbenzoate.

The 2-butyl-3-(4-(1-cyanomethyl-4,5-dichloro-2-imidazolyl)-benzyl)-4,5-dihydro-4-oxo-5-$R^3$-3H-IPs below are obtained analogously:

| | |
|---|---|
| with methyl iodide: | -5-methyl- |
| with isopropyl bromide: | -5-isopropyl- |
| with butyl bromide: | -5-butyl- |
| with trifluoromethyl iodide: | -5-trifluoromethyl- |
| with bromoacetic acid: | -5-carboxymethyl- |
| with methyl bromoacetate: | -5-methoxycarbonyl-methyl- |
| with ethyl bromoacetate: | -5-ethoxycarbonyl-methyl- |
| with phenyl bromoacetate: | -5-phenoxycarbonyl-methyl- |
| with bromoacetamide: | -5-carbamoylmethyl- |
| with N-methylbromoacetamide: | -5-(N-methyl-carbamoylmethyl)- |
| with N,N-dimethylchloroacetamide: | -5-(N,N-dimethyl-carbamoylmethyl)- |
| with N,N-diethylchloroacetamide: | -5-(N,N-diethyl-carbamoylmethyl)- |
| with chloroacetanilide: | -5-(N-phenylcarbamoyl-methyl)- |
| with chloroacetic acid(2,6-dimethylanilide): | -5-(N-(2,6-dimethyl-phenyl)carbamoyl-methyl)- |
| with N-methyl-N-phenyl-chloroacetamide: | -5-(N-methyl-N-phenylcarbamoyl-methyl)- |
| with bromoacetone: | -5-(2-oxopropyl)- |
| with 1-bromo-3,3-dimethyl-2-butanone: | -5-2-oxo-3,3-dimethylbutyl)- |
| with 2-dimethylaminoethyl chloride: | -5-(2-dimethylamino-ethyl)- |
| with 2-anilinoethyl chloride: | -5-(2-anilinoethyl)- |
| with cyclopropylmethyl bromide: | -5-cyclopropylmethyl- |
| with cyclobutylmethyl chloride: | -5-cyclobutylmethyl- |
| with cyclopentylmethyl chloride: | -5-cyclopentylmethyl- |
| with cyclohexylmethyl chloride: | -5-cyclohexylmethyl- |
| with benzyl bromide: | -5-benzyl- |
| with 2-fluorobenzyl bromide: | -5-(2-fluorobenzyl)- |
| with 2-chlorobenzyl bromide: | -5-(2-chlorobenzyl)- |
| with 2-bromomethylbenzoic acid | -5-(2-carboxybenzyl)- |
| with ethyl 2-bromomethyl-benzoate: | -5-(2-ethoxycarbonyl-benzyl)- |
| with 2-nitrobenzyl chloride: | -5-(2-nitrobenzyl)- |

-continued

| | |
|---|---|
| with 2-dimethylaminobenzyl chloride: | -5-(2-dimethylamino-benzyl)- |
| with 2-acetamidobenzyl chloride: | -5-(2-acetamido-benzyl)- |
| with 4-methoxybenzyl chloride: | -5-(4-methoxy-benzyl)- |
| with 2-thienylmethyl chloride: | -5-(2-thienylmethyl)- |
| with phenacyl bromide: | -5-phenacyl- |
| with 2-methoxyphenacyl chloride: | -5-(2-methoxy-phenacyl)- |
| with 2-oxo-2-(2-pyridyl)ethyl-chloride: | -5-(2-oxo-2-(2-pyridyl)ethyl)-. |

(b) Analogously to Example 4(b), the 2-butyl-3-(4-(1-(1H-5-tetrazolylmethyl)-4,5-dichloro-2-imidazolyl)benzyl-4,5-dihydro-4-oxo-5-$R^3$3H-IPs below are obtained from the 1-cyanomethyl-4,5-dichloro-2-imidazolyl compounds given in (a) using trimethyltin azide:

-5-methyl-
-5-isopropyl-
-5-butyl-
-5-trifluoromethyl-
-5-carboxymethyl-
-5-methoxycarbonylmethyl-
-5-ethoxycarbonylmethyl-
-5-phenoxycarbonylmethyl-
-5-carbamoylmethyl-
-5-(N-methylcarbamoylmethyl)-
-5-(N,N-dimethylcarbamoylmethyl)-
-5-(N,N-diethylcarbamoylmethyl)-
-5-(N-phenylcarbamoylmethyl)-
-5-(N-(2,6-dimethylphenyl)carbamoylmethyl)-
-5-(N-methyl-N-phenylcarbamoylmethyl)-
-5-(2-oxopropyl)-
-5-(2-oxo-3,3-dimethylbutyl)-
-5-(2-dimethylaminoethyl)-
-5-(2-anilinoethyl)-
-5-cyclopropylmethyl-
-5-cyclobutylmethyl-
-5-cyclopentylmethyl-
-5-cyclohexylmethyl-
-5-benzyl-
-5-(2-fluorobenzyl)-
-5-(2-chlorobenzyl)-
-5-(2-carboxybenzyl)-
-5-(2-ethoxycarbonylbenzyl)-
-5-(2-nitrobenzyl)-
-5-(2-dimethylaminobenzyl)-
-5-(2-acetamidobenzyl)-
-5-(4-methoxybenzyl)-
-5-(2-thienylmethyl)-
-5-phenacyl-
-5-(2-methoxyphenacyl)-
-5-(2-oxo-2-(2-pyridyl)ethyl)-

Example 7

(a) Analogously to Example 4(a), 2-butyl-3-(4-(1ethoxycarbonylmethyl-2-imidazolyl)benzyl)-4,5-dihydro-4-oxo-5-(2-methoxycarbonyl-benzyl)-3H-IP is obtained from 2-butyl-3-(4-(1-ethoxycarbonylmethyl-2-imidazolyl)benzyl)-4,5-dihydro-4-oxo-3H-IP and methyl 2-bromomethyl benzoate.

The 2-butyl-3-(4-(1-ethoxycarbonylmethyl-2-imidazolyl)benzyl)-4,5-dihydro-4-oxo-5-$R^3$-3H-IPs below are obtained analogously:

| | |
|---|---|
| with methyl iodide: | -5-methyl- |
| with isopropyl bromide: | -5-isopropyl- |
| with butyl bromide: | -5-butyl- |
| with trifluoromethyl iodide: | -5-trifluoromethyl- |
| with bromoacetic acid: | -5-carboxymethyl- |
| with methyl bromoacetate: | -5-methoxycarbonylmethyl- |
| with ethyl bromoacetate: | -5-ethoxycarbonylmethyl- |
| with phenyl bromoacetate: | -5-phenoxycarbonylmethyl- |
| with bromoacetamide: | -5-carbamoylmethyl- |
| with N-methylbromoacetamide: | -5-(N-methylcarbamoylmethyl)- |
| with N,N-dimethylchloroacetamide: | -5-(N,N-dimethylcarbamoylmethyl)- |
| with N,N-diethylchloroacetamide: | -5-(N,N-diethylcarbamoylmethyl)- |
| with chloroacetanilide: | -5-(N-phenylcarbamoyl-methyl)- |
| with chloroacetic acid(2,6-dimethylanilide): | -5-(N-(2,6-dimethylphenyl)carbamoylmethyl)- |
| with N-methyl-N-phenyl-chloroacetamide: | -5-(N-methyl-N-phenylcarbamoylmethyl)- |
| with bromoacetone: | -5-(-2-oxopropyl)- |
| with 1-bromo-3,3-dimethyl-2-butanone: | -5-2-oxo-3,3-dimethylbutyl)- |
| with 2-dimethylaminoethyl chloride: | -5-(2-dimethylaminoethyl)- |
| with 2-anilinoethyl chloride: | -5-(2-anilinoethyl)- |
| with cyclopropylmethyl bromide: | -5-cyclopropylmethyl- |
| with cyclobutylmethyl chloride: | -5-cyclobutylmethyl- |
| with cyclopentylmethyl chloride: | -5-cyclopentylmethyl- |
| with cyclohexylmethyl chloride: | -5-cyclohexylmethyl- |
| with benzyl bromide: | -5-benzyl- |
| with 2-fluorobenzyl bromide: | -5-(2-fluorobenzyl)- |
| with 2-chlorobenzyl bromide: | -5-(2-chlorobenzyl)- |
| with 2-bromomethylbenzoic acid | -5-(2-carboxybenzyl)- |
| with ethyl 2-bromomethylbenzoate: | -5-(2-ethoxycarbonylbenzyl)- |
| with 2-nitrobenzyl chloride: | -5-(2-nitrobenzyl)- |
| with 2-dimethylaminobenzyl chloride: | -5-(2-dimethylaminobenzyl)- |
| with 2-acetamidobenzyl chloride: | -5-(2-acetamidobenzyl)- |
| with 4-methoxybenzyl chloride: | -5-(2-4-methoxybenzyl)- |
| with 2-thienylmethyl chloride: | -5-(2-thienylmethyl)- |
| with phenacyl bromide: | -5-phenacyl- |
| with 2-methoxyphenacyl chloride: | -5-(2-methoxyphenacyl)- |
| with 2-oxo-2-(2-pyridyl)ethyl chloride: | -5-(2-oxo-2-(2-pyridyl)ethyl)-. |

(b) A mixture of 1 g of 2-butyl-3-(4-(1-ethoxycarbonylmethyl-2-imidazolyl)benzyl)-4,5-dihydro-4-oxo-5-(2-methoxycarbonylbenzyl)-3H-IP, 12 ml of aqueous 2n NaOH solution and 48 ml of methanol is boiled for 2 hours, then evaporated. The residue is worked up in the conventional manner (aqueous hydrochloric acid to pH 3/dichloromethane) and gives 2-butyl-3-(4-(1-carboxymethyl-2-imidazolyl)-benzyl)-4,5-dihydro-4-oxo-5-(2-carboxybenzyl)-3H-IP.

Analogously, the 2-butyl-3-(4-(1-carboxymethyl-2-imidazolyl)benzyl-4,5-dihydro-4-oxo-5-R3-3H-IPs are obtained by hydrolysis of the esters given above in (a):
-5-methyl-
-5-isopropyl-
-5-butyl-
-5-trifluoromethyl-
-5-carboxymethyl-
-5-methoxycarbonylmethyl-
-5-ethoxycarbonylmethyl-
-5-phenoxycarbonylmethyl-
-5-carbamoylmethyl-
-5-(N-methylcarbamoylmethyl)-
-5-(N, N-dimethylcarbamoylmethyl)-
-5-(N, N-diethylcarbamoylmethyl)-
-5-(N-phenylcarbamoylmethyl)-
-5-(N-(2,6-dimethylphenyl)carbamoylmethyl)-
-5-(N-methyl-N-phenylcarbamoylmethyl)-
-5-(2-oxopropyl)-
-5-(2-oxo-3,3-dimethylbutyl)-
-5-(2-dimethylaminoethyl)-
-5-(2-anilinoethyl)-
-5-cyclopropylmethyl-
-5-cyclobutylmethyl-
-5-cyclopentylmethyl-
-5-cyclohexylmethyl-
-5-benzyl-
-5-(2-fluorobenzyl)-
-5-(2-chlorobenzyl)-
-5-(2-carboxybenzyl)-
-5-(2-ethoxycarbonylbenzyl)-
-5-(2-nitrobenzyl)-
-5-(2-dimethylaminobenzyl)-
-5-(2-acetamidobenzyl)-
-5-(4-methoxybenzyl)-
-5-(2-thienylmethyl)-
-5-phenacyl-
-5-(2-methoxyphenacyl)-
-5-(2-oxo-2-(2-pyridyl)ethyl)-

Example 8

(a) Analogously to Example 4(a), 2-butyl-3-(4-(1-ethoxycarbonylmethyl-4,5-dichlor-2-imidazolyl)-benzyl)-4,5-dihydro-4-oxo-5-(2-methoxycarbonylbenzyl)-3H-IP is obtained from 2-butyl-3-(4-(1-ethoxycarbonylmethyl-4,5-dichlor-2-imidazolyl)-benzyl)-4,5-dihydro-4-oxo-3H-IP and methyl 2-bromomethylbenzoate.

The 2-butyl-3-(4-(1-ethoxycarbonylmethyl-4,5-dichlor-2-imidazolyl)benzyl)-4,5-dihydro-4-oxo-5-$R^3$-3H-IPs below are obtained analogously:

| | |
|---|---|
| with methyl iodide: | -5-methyl- |
| with isopropyl bromide: | -5-isopropyl- |
| with butyl bromide: | -5-butyl- |
| with trifluoromethyl iodide: | -5-trifluoromethyl- |
| with bromoacetic acid: | -5-carboxymethyl- |
| with methyl bromoacetate: | -5-methoxycarbonylmethyl- |
| with ethyl bromoacetate: | -5-ethoxycarbonylmethyl- |
| with phenyl bromoacetate: | -5-phenoxycarbonylmethyl- |
| with bromoacetamide: | -5-carbamoylmethyl- |
| with N-methylbromoacetamide: | -5-(N-methylcarbamoylmethyl)- |
| with N,N-dimethylchloroacetamide: | -5-(N,N-dimethylcarbamoylmethyl)- |
| with N,N-diethylchloroacetamide: | -5-(N,N-diethylcarbamoylmethyl)- |
| with chloroacetanilide: | -5-(N-phenylcarbamoyl-methyl)- |
| with chloroacetic acid-(2,6-dimethylanilide): | -5-(N-(2,6-dimethylphenyl)carbamoylmethyl)- |
| with N-methyl-N-phenyl-chloroacetamide: | -5-(N-methyl-N-phenylcarbamoylmethyl)- |
| with bromoacetone: | -5-(2-oxopropyl)- |
| with 1-bromo-3,3-dimethyl-2-butanone: | -5-2-oxo-3,3-dimethylbutyl)- |
| with 2-dimethylaminoethyl chloride: | -5-(2-dimethylaminoethyl)- |
| with 2-anilinoethyl chloride: | -5-(2-anilinoethyl)- |

| | |
|---|---|
| with cyclopropylmethyl bromide: | -5-cyclopropylmethyl- |
| with cyclobutylmethyl chloride: | -5-cyclobutylmethyl- |
| with cyclopentylmethyl chloride: | -5-cyclopentylmethyl- |
| with cyclohexylmethyl chloride: | -5-cyclohexylmethyl- |
| with benzyl bromide: | -5-benzyl- |
| with 2-fluorobenzyl bromide: | -5-(2-fluorobenzyl)- |
| with 2-chlorobenzyl bromide: | -5-(2-chlorobenzyl)- |
| with 2-bromomethylbenzoic acid | -5-(2-carboxybenzyl)- |
| with ethyl 2-bromomethyl-benzoate: | -5-(2-ethoxycarbonyl-benzyl)- |
| with 2-nitrobenzyl chloride: | -5-(2-nitrobenzyl)- |
| with 2-dimethylaminobenzyl chloride: | -5-(2-dimethylamino-benzyl)- |
| with 2-acetamidobenzyl chloride: | -5-(2-acetamido-benzyl)- |
| with 4-methoxybenzyl chloride: | -5-(2-4-methoxy-benzyl)- |
| with 2-thienylmethyl chloride: | -5-(2-thienylmethyl)- |
| with phenacyl bromide: | -5-phenacyl- |
| with 2-methoxyphenacyl chloride: | -5-(2-methoxy-phenacyl)- |
| with 2-oxo-2-(2-pyridyl)ethyl chloride: | -5-(2-oxo-2-(2-pyridyl)ethyl)-. |

(b) Analogously to Example 7(b), 2-butyl-3-(4-(1-carboxymethyl-4,5-dichlor-2-imidazolyl)benzyl)-4,5-dihydro-4-oxo-5-(2-carboxybenzyl)-3H-IP is obtained by hydrolysis of 2-butyl-3-(4-(1-ethoxycarbonylmethyl-4,5-dichlor-2-imidazolyl)benzyl)-4,5-dihydro-4-oxo-5-(2-methoxycarbonylbenzyl)-3H-IP.

The 2-butyl-3-(4-(1-carboxymethyl-4,5-dichlor-2-imidazolyl)benzyl-4,5-dihydro-4-oxo-5-R$^3$-3H-IPs below are obtained analogously by hydrolysis of the esters given above in (a):
-5-methyl-
-5-isopropyl-
-5-butyl-
-5-trifluoromethyl-
-5-carboxymethyl-
-5-methoxycarbonylmethyl-
-5-ethoxycarbonylmethyl-
-5-phenoxycarbonylmethyl-
-5-carbamoylmethyl-
-5-(N-methylcarbamoylmethyl)-
-5-(N,N-dimethylcarbamoylmethyl)-
-5-(N,N-diethylcarbamoylmethyl)-
-5-(N-phenylcarbamoylmethyl)-
-5-(N-(2,6-dimethylphenyl)carbamoylmethyl)-
-5-(N-methyl-N-phenylcarbamoylmethyl)-
-5-(2-oxopropyl)-
-5-(2-oxo-3,3-dimethylbutyl)-
-5-(2-dimethylaminoethyl)-
-5-(2-anilinoethyl)-
-5-cyclopropylmethyl-
-5-cyclobutylmethyl-
-5-cyclopentylmethyl-
-5-cyclohexylmethyl-
-5-benzyl-
-5-(2-fluorobenzyl)-
-5-(2-chlorobenzyl)-
-5-(2-carboxybenzyl)-
-5-(2-ethoxycarbonylbenzyl)-
-5-(2-nitrobenzyl)-
-5-(2-dimethylaminobenzyl)-
-5-(2-acetamidobenzyl)-
-5-(4-methoxybenzyl)-
-5-(2-thienylmethyl)-
-5-phenacyl-
-5-(2-methoxyphenacyl)-
-5-(2-oxo-2-(2-pyridyl)ethyl)-

Example 9

Analogously to Example 7(b), 2-butyl-3-(4-2-(1H-5-tetrazolyl)-3-thienyl)benzyl)-4,5-dihydro-4-oxo-5-(2-carboxybenzyl)-3H-IP is obtained by hydrolysis of 2-butyl-3-(4-(2-(1H-5-tetrazolyl)-3-thienyl)benzyl)-4,5-dihydro-4-oxo-5-(2-methoxycarbonylbenzyl)-3H-IP.

Analogously, hydrolysis of the corresponding methyl or ethyl esters indicated in Examples 4–6 gives the carboxylic acids also indicated there.

Example 10

A solution of 1 g of 2-butyl-3-(4-(2-(1H-5-tetrazolyl)-3-thienyl)benzyl)-4,5-dihydro-4-oxo-5-(2-nitrobenzyl)-3H-IP in 20 ml of methanol is hydrogenated on 0.3 g of 5% Pd-carbon at 20° and normal pressure until the calculated amount of $H_2$ has been absorbed. The catalyst is filtered off, the filtrate is evaporated and 2-butyl-3-(4-(2-(1H-5-tetrazolyl)-3-thienyl)benzyl)-4,5-dihydro-4-oxo-5-(2-aminobenzyl)-3H-IP is obtained.

Example 11

A solution of 1 g of 2-butyl-3-(4-(2-(1H-5-tetrazolyl)-3-thienyl)benzyl)-4,5-dihydro-4-oxo-5-(6-BOC-aminohexyl)-3H-IP in 20 ml of dichloromethane and 20 ml of trifluoroacetic acid is stirred for 1 hour at 20° and evaporated, and the residue is worked up in the conventional manner. 2-Butyl-3-(4-(2-(1H-5-tetrazolyl)-3-thienyl)benzyl)-4,5-dihydro-4-oxo-5-(6-aminohexyl)-3H-IP is obtained.

The following examples relate to pharmaceutical formulations containing the active ingredients of formula I or their salts.

Example A: Tablets and Coated Tablets

Tablets of the following composition are produced by compression in the conventional manner and, where required, are provided with a conventional sucrose-based coating:

| | |
|---|---|
| Active ingredient of formula I | 100 mg |
| Microcrystalline cellulose | 278.8 mg |
| Lactose | 110 mg |
| Maize starch | 11 mg |
| Magnesium stearate | 5 mg |
| Finely divided silicon dioxide | 0.2 mg |

Example B: Hard Gelatin Capsules

Conventional two-part hard gelatin capsules are each filled with

| | |
|---|---|
| Active ingredient of formula I | 100 mg |
| Lactose | 150 mg |
| Cellulose | 50 mg |
| Magnesium stearate | 6 mg |

Example C: Soft Gelatin Capsules

Conventional soft gelatin capsules are filled with a mixture of 50 mg of active ingredient and 250 mg of olive oil in each case.

Example D: Ampoules

A solution of 200 g of active ingredient in 2 kg of propane-1,2-diol is made up to 10 l with water and filled into ampoules so that each ampoule contains 20 mg of active ingredient.

Example E: Aqueous Suspension for Oral Administration

An aqueous suspension of the active ingredient is prepared in the conventional manner. The unit dose (5 ml) contains 100 mg of active ingredient, 100 mg of Na-carboxymethylcellulose, 5 mg of Na-benzoate and 100 mg of sorbitol.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazopyridine derivative of formula I

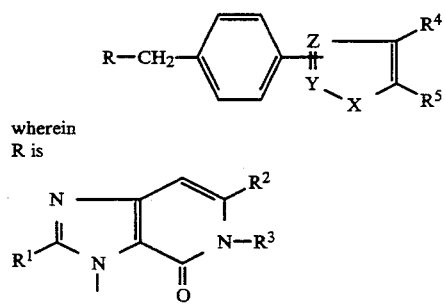

wherein R is

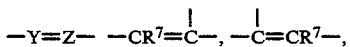

is O, S or $NR^6$,

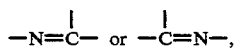

$R^1$ is A, alkenyl or alkynyl each having up to 6 C atoms, cycloalkyl having 3–7 C atoms, OA or SA, $R^2$ is H or Hal, $R^3$ is $-C_nH_{2n}-R^9$, $R^4$ and $R^5$ are each H, A or Hal, $R^6$ is H or $-C_mH_{2m}-R^{10}$, $R^7$ and $R^{10}$ are each CN, $COOR^{11}$ or 1H-5-tetrazolyl, $R^8$ is alkyl having 1–6 C atoms, wherein one or more H atoms can also be replaced by F, $R^9$ is $COOR^{12}$, $CONR^{12}R^{13}$, COA, $NR^{12}R^{13}$, cycloalkyl having 3–7 C atoms, Ar, or COAr, $R^{11}$, $R^{12}$ and $R^{13}$ are each H, A or Ar, A is alkyl having 1–6 C atoms, Ar is an unsubstituted phenyl group or a phenyl group monosubstituted or disubstituted by $R^8$, OH, $OR^8$, COOH, COOA, CN, $NO_2$, $NH_2$, $NHCOR^8$, $NHSO_2R^8$, Hal or 1H-tetrazol-5-yl, Het is a five- or six-membered heteroaromatic radical having 1 to 3N, O and/or S atoms, which can also be substituted one or more times by A and/or can be fused to a benzene or pyridine ring, Hal is F, Cl, Br or I and, m and n are each 1, 2, 3, 4, 5 or 6, and its salts.

2. Imidazopyridine derivatives:
   a) 2-butyl-3-(4-(2-cyano-3-thienyl)benzyl)-4,5-dihydro-4-oxo-3H-imidazo[4,5-c]pyridine;
   b) 2-butyl-3-(4-(2-cyano-3-thienyl)benzyl-4,5-dihydro-4-oxo-5-(2-methoxycarbonylbenzyl)-3H-imidazo[4,5-c]pyridine; and
   c) 2-butyl-3-(4-(2-(1H-5-tetrazolyl)-3-thienyl)benzyl)-4,5-dihydro-4-oxo-5-(2-methoxycarbonylbenzyl)-3H-imidazo[4,5-c]pyridine.

3. A process for the preparation of pharmaceutical formulations, wherein a compound of formula I according to claim 1, and/or one of its physiologically acceptable acid addition salts are incorporated into a suitable dosage form together with at least one solid, liquid or semiliquid excipient or adjunct.

4. A method for treating angiotensin(II)-dependent diseases or conditions, comprising administering an effective amount of a compound of the formula I and/or a physiologically acceptable acid addition salt thereof to a patient with such a disease or condition.

5. A method as in claim 4, wherein said disease is angiotensin(II)-dependent hypertension.

* * * * *

UNITED STATES PATENT AND TRADEMARK OFFICE
CERTIFICATE OF CORRECTION

PATENT NO. : 5,405,964
DATED : April 11, 1995
INVENTOR(S) : Werner MEDERSKI et al.

It is certified that error appears in the above-indentified patent and that said Letters Patent is hereby corrected as shown below:

Claim 1; column 21, line 38: Before is insert --X--.

Signed and Sealed this

Tenth Day of October, 1995

Attest:

BRUCE LEHMAN

Attesting Officer

Commissioner of Patents and Trademarks